US007179609B1

(12) United States Patent
Mårdh et al.

(10) Patent No.: US 7,179,609 B1
(45) Date of Patent: Feb. 20, 2007

(54) SCREENING METHOD FOR GASTRITIS (75) Inventors: Sven Mårdh, Vreta Kloster (SE); Erik Mårdh, Vreta Kloster (SE)

(73) Assignee: Atrophus AB, Linkoping (SE)

( * ) Notice: Subject to any disclaimer, the term of this patent is extended or adjusted under 35 U.S.C. 154(b) by 0 days.

(21) Appl. No.: 09/678,357

(22) Filed: Oct. 4, 2000

(51) Int. Cl.
*G01N 33/53* (2006.01)
*G01N 33/567* (2006.01)
*G01N 33/554* (2006.01)
*C12Q 1/58* (2006.01)
*A61K 39/02* (2006.01)

(52) U.S. Cl. .................. 435/7.2; 435/7.21; 435/7.32; 435/12; 435/252.1; 424/234.1

(58) Field of Classification Search .............. 424/9.1, 424/9.2, 130.1, 164.1, 234.1; 435/4, 7.1, 435/7.2, 7.32, 12, 252.1, 7.21, 501
See application file for complete search history.

(56) References Cited

U.S. PATENT DOCUMENTS

| | | | |
|---|---|---|---|
| 4,830,010 A | 5/1989 | Marshall | |
| 5,364,793 A | 11/1994 | Cameron, Sr. et al. | |
| 5,524,622 A | 6/1996 | Wilson | |
| 5,814,455 A | 9/1998 | Pronovost et al. | |
| 5,879,897 A | 3/1999 | Koufman | |
| 5,932,430 A * | 8/1999 | Larka et al. | 435/7.32 |
| 5,989,840 A * | 11/1999 | D'Angelo et al. | 435/7.32 |
| 6,067,989 A | 5/2000 | Katzman | |
| 6,068,985 A | 5/2000 | Cripps et al. | |
| 6,090,611 A | 7/2000 | Covacci et al. | |

FOREIGN PATENT DOCUMENTS

WO   WO 96/15456   *   5/1996

OTHER PUBLICATIONS

Lindgren et al. , "Serum antibodies to H, K- ATP ase, serum pepsinogen A and *Helicobacter pylori* in relation to gastric mucosa . . . " European Journal of Gastroenterology and Hepatology, vol. 10, No. 7, pp. 583-588. Jul. 1998.*
Applemelk,BJ et al. "*Helicobacter pylori* associated autoantibodies recognize Lewis antigens, and peptide epitopes of gastric H,K-ATPase and intrinsic factor", Gut vol. 41(suppl. 1) p. A17, Sep. 1997.*
Oksanen, A. et al. "Evaluation of Pyloriset Screen, A Rapid Whole-Blood Diagnostic Test for *Helicobacter pylori* Infection", Journal of Clinical Microbiology, vol. 36, No. 4, pp. 955-957, Apr. 1998.*
Matsumoto,K et al. , "Association between *Helicobacter pylori* infectionand serum pepsinogen concentration in gastroduodenal disease.", Journal of Clinical Pathology, vol. 49, No. 12, pp. 1005-1008,1996.*
Oksanen, A. et al. "Evaluation of blood tests to predict normal gastric mucosa"., Scandinavian Journal of Gastroenterology, vol. 35, No. 8 pp. 791-795, Aug. 2000.*
Ma J Y et al. "Positive Correlation between H,K-Adenosine Triphosphatase Autoantibodies and *Helicobacter pylori* Antibodies in Patients with Pernicious Anemia.", Scandinavian Journal of Gastroenterology, vol. 29, No. 11, pp. 961-965, 1994.*
Shih et al. ("Enzyme -linked immunoabsobent assays for serum pepsinogens I And II . . . ,"), Clininca Chemica Acta, vol. 175, pp. 37-50, 1988.*
Lindgren et al. , "Serum antibodies to H, K- ATP ase, serum pepsinogen A and *Helicobacter pylori* in relation to gastric mucosa . . . " European Journal of Gastroenterology and Hepatology, vol. 10, No. 7, pp. 583-588 , Jul. 1998.*
Oksanen, A. et al. "Evaluation of blood tests to predict normal gastric mucosa"., Scandinavian Journal of Gastroenterology, vol. 35, No. 8 pp. 791-795, Aug. 2000.*
Ma J Y et al. "Positive Correlation between H,K-Adenosine Triphosphatase Autoantibodies and *Helicobacter pylori* Antibodies in Patients with Pernicious Anemia.", Scandinavian Journal of Gastroenterology, vol. 29, No. 11, pp. 961-965 , 1994.*
Lin et al. ,Journal of Gastroenterology vol. 30, pp. 156-161, 1995.*
Medicine Net.com : Definition of Antrum.*
Wikipedia: Definition of Antrum.*
Harris A, Dyspepsia and *Helicobacter pylori*: test, treat or investigate? Eur J Gastroenterol Hepat 1999; 11 (Suppl 1): S31-5.
Working Party of the Clinical Services Committee of the British Society of Gastroenterology. Provision of gastrointestinal endoscopy and related serices for a district general hospital. Gut 1991; 32: 95-105.
Gear MWL, Wilkinson SP, Open access upper alimentary endoscopy. Br J Hosp Med 1989; 41: 438-44.
Bodger K, Wyatt JI, Heatley RV, Serologic screening before endoscopy: The value of *Helicobacter pylori* serology, serum recognition of the CagA and VacA proteins, and serum pepsinogen I, Scand J Gastroenterol 1999; 34: 856-63.
Moayyedi P, Zilles A, Clough M, Hemingbrough E, Chalmers DM, Axon AT, The effectiveness of screening and treating *Helicobacter pylori* in the management of dyspepsia, Eur J Gastroenterol Hepatol 1999; 11:1245-50.
Chiba N, Lahaie R, Fedorak RN, Bailey R, Veldhuyzen van Zanten SJ, Bernucci B, *Helicobacter pylori* and peptic ulcer disease. Current evidence for management strategies, Can Fam Physician 1998; 44: 1481-8.

(Continued)

*Primary Examiner*—Larry R. Helms
*Assistant Examiner*—Khatol Shahnan-Shah
(74) *Attorney, Agent, or Firm*—Marina Larson & Associates LLC (57) ABSTRACT

A screening method for gastritis is provided. The method involves the serological measurement of at least two of the following analytes: H,K-ATPase antibodies, *Helicobacter pylori* antibodies and the concentration of pepsinogen I; and the evaluation of the results in comparison with results from normal individuals. The evaluation scheme provides an initial, non-invasive identification of individuals with various forms of gastritis.

12 Claims, 4 Drawing Sheets

OTHER PUBLICATIONS

Genta RM, Acid suppression and gastric atrophy: sifting fact from fiction, Gut 1998; 43: 35-8, Suppl. 1.

Iseld K. et al, *Helicobacter pylori* infection in patients with early gastric cancer by endoscopic phenol red test, Gastrointest Endosc 1998; 48: 327-8.

Lee BM, Jang JJ, Kim JS, You YC, Chun SA, Kim HS, et al., Association of *Heliconacter pylori* infection with gastric adenocarcinoma, Jpn J Cancer Res 1998; 89: 597-603.

Ozasa K, Kurata JH, Higashi A, K. Hayashi K, Inokuchi H, Miki K, et al., *Helicobacter pylori* infection and atrophic gastritis: a nested case-control study in a rural town in Japan, Dig Dis Sci 1999; 44:253-6.

Bech K, Hoier-Madsen M, Feldt-Rasmussen U, Jensen BM, Molsted-Pedersen L, Kuhl C, Thyroid function and autoimmune manifestations in insulin-dependent diabetes mellitus during and after pregnancy, Acta Endocrinol 1991; 124: 534-9.

Barrio R, Roldan MB, Alonso M, Canton R, Camarero C, *Helicobacter pylori* infection with parietal cell antibodies in children and adolescents with insulin dependent diabetes mellitus, Pediatr Endocrinol Metab 1997; 10: 511-6.

Datta A, Deodhar SD, Datta U, Sehgal S, Non-organ specific & organ specific antibodies in rheumatoid arthritis, Indian J Med Res 1990; 92: 228-32.

Mårdh S, Ma JY, Song YH, Aly A, Henriksson K, Occurrence of autoantibodies against intrinsic factor, H,K-ATPase and pepsinogen in atrophic gastritis and rheumatoid arthritis. Scand J Gastroenterol 1991; 26: 1089-96.

Karlsson A, Burman P, Lööf L, Mårdh S, Major parietal cell antigen in autoimmune gastritis with pernicious anemia is the acid-producing H,K-adenosine triphosphatase of the stomach, J Clin Invest 1988; 81: 475-9.

Song YH, Ma JY, Mårdh S, Liu T, Sjöstrand SE, Rask L et al., Localization of a pernicious anemia-autoantibody epitope on the a-subunit of the human H,K-ATPase Scand J Gastroenterol 1994; 29: 122-7.

Baron JH, Clinical tests of gastric secretion: History, Methodology and Interpretation. (1978) London: Macmillan.

Samloff IM, Varis K, Ihamaki T, Siurala M, Rotter JI, Relationships among serum pepsinogen I, serum pepsinogen II, and gastric mucosal histology. A study in relatives of patients with pernicious anemia. Gastroenterol Jul. 1982; 83(1 Pt 2): 204-9.

Borch K, Stridsberg M, Burman P, Rehfeld JF, Basal chromogranin A and gastrin concentrations in circulation correlate to endocrine cell proliferation in type A gastritis. Scand J Gastroenterol 1997; 32:198-202.

Carmel R, Pepsinogens and other serum markers in pernicious anemia. Am J of Clinical Pathol 1998; 90: 442-5.

Waters HM, Smith C, Howarth JE, Dawson DW, Delamore IW, New enzyme immunoassay for detecting total, type I, and type II intrinsic factor antibodies. J Clin Pathol 1989; 42: 307-12.

Borch K, Liedberg G, Prevalence and incidence of pernicious anemia. An evaluation for gastric screening. Scand J Gastroenterol 1984; 19: 154-60.

Borch K, Jönsson KÅ, Redéen S, Petersson F, Mårdh S, Franzén L, Prevalence of gastroduodenitis and *Helicobacter pylori* infection in the general population: Relations to symptomatology and life style. Dig Dis Sci, 2000, 45: 1322-29.

Price A, The Sydney system: Histological division, J Gastroenterol Hepatol 1991; 6: 209-22.

Dixon MF, Genta RM, Yardley JH, Correa P, the Participants in the International Workshop on the Histopathology of Gastritis, Houston 1994. Classification and grading of gastritis. The updated Sydney system, Am J Surg Pathol 1996; 20: 1161-81.

Karlsson FA, Burman P, Lööf L, Olsson M, Scheynius A, Mårdh S, Enzyme-linked immunosorbent assay of H,K-ATPase, the parietal cell antigen. Clin exp Immunol 1987; 70:604-10.

Ma J-Y; Borch K, Sjöstrand SE, Janzon L, Mårdh S, Positive correlation between H,K-adenosine triphosphatase autoantibodies and *Helicobacter pylori* antibodies in patients with pernicious anemia. Scand J Gastroenterol 1994; 29: 961-6.

\* cited by examiner

SCREENING METHOD FOR GASTRITIS

BACKGROUND OF THE INVENTION

Dyspepsia, or indigestion, is a common diagnosis in primary health care, but with poorly defined management. The annual prevalence of dyspepsia in the United Kingdom (UK) is about 25%, and in primary health care it accounts for 3–4% of the consultations (Harris, A., Eur J Gastroenterol Hepat 1999; 11 (Suppl 1): S31–5). Among the chronic disorders of the upper gastrointestinal tract are those which fall under the general category of gastritis. Gastritis is an inflammation of the stomach mucosa which is manifested by a broad range of poorly-defined symptoms such as indigestion, "heart burn" and excessive eructation. The typical means used to diagnose gastrointestinal disorders depends on such factors as the nature and severity of symptoms, the overall health of the individual, the medical history of the patient, the need for a specific diagnosis in order to implement a treatment with reasonable likelihood of success, and the availability of diagnostic devices.

Esophagogastroduodenoscopy (EGD) with histopathological examination of biopsies is the gold standard to determine the status of the gastric and duodenal mucosa. This examination is safe, accurate and sometimes indispensable, e.g., in the older age group and especially in the presence of alarm symptoms such as weight loss, anorexia, dysphagia, or gastrointestinal blood loss. The demand for upper endoscopy is increasing and in the UK approximately 0.5% of the population undergo this examination each year (Working Party of the Clinical Services Committee of the British Society of Gastroenterology, Provision of gastrointestinal endoscopy and related services for a district general hospital. Gut 1991; 32: 95–105; Gear, M. W. L., and Wilkinson, S. P., Br J Hosp Med 1989; 41: 438–44). Without EGD and visual inspection of the mucosa, gastritis is difficult to diagnose. However, EGD is expensive, inconvenient for the patient, and generally not recommended for children or patients with severe cardiopulmonary disease. Thus, for patients not having severe symptoms, a precise diagnosis of a gastrointestinal disorder might not be attempted. Such patients may simply be treated with conventional therapies, such as with antacids or drugs which inhibit stomach acid secretion. While such therapies might provide temporary relief of the symptoms, a cure is not often achieved. More effective treatments generally depend on a better diagnosis of the actual underlying gastrointestinal disorder. For example, many gastrointestinal disorders are mediated by bacterial infection of the mucosa, in which case treatment of the bacterial infection would most likely be required to effectively treat the manifested gastrointestinal disorder.

There is a need for a simple pre-gastroscopic screening method to reduce the endoscopy workload, and attempts have been made in this direction with some success in patients with uncomplicated simple dyspepsia (Bodger, K., et al., Scand J Gastroenterol 1999; 34: 856–63; and Moayyedi, P., et al., Eur J Gastroenterol Hepatol 1999; 11:1245–50). In young dyspeptic patients (<40 years) screening for Helicobacter pylori (H. pylori) infection and a treatment strategy based on the presence of an infection reduces the endoscopy workload. This strategy appears as effective as an endoscopy-based strategy in reducing dyspeptic symptoms, dyspepsia consultation rates and the prescription of anti-secretory drugs (Moayyedi, P., et al., Eur J Gastroenterol Hepatol 1999; 11:1245–50). In the elderly with dyspepsia, however, the prevalence of gastritis and its consequences are considerably higher pointing at EGD as the initial diagnostic step.

The inflamed gastric mucosa transmits specific information to the blood stream that allows diagnosis of gastritis by serologic analysis. The morphology and cellular composition of the mucosa vary between the acid secreting corpus and the antrum. This may aid to distinguish corpus and pangastritis from antral gastritis. A number of serological markers have been described. Infection with H. pylori is the major cause of chronic gastritis, duodenal ulcer, mucosa associated lymphoid tissue (MALT) lymphoma and gastric cancer (Chiba, N., et al., Can Fam Physician 1998; 44: 1481–8; Genta, R. M., Gut 1998; 43: 35–8; Coyle, W. J., et al., Gastrointest Endosc 1998; 48: 327–8; Lee, B. M., et al., Jpn J Cancer Res 1998; 89: 597–603), and antibodies to various H. pylori antigens can easily be detected in the blood (Bodger, K., et al., Scand J Gastroenterol 1999; 34: 856–63; Moayyedi, P., et al., Eur J Gastroenterol Hepatol 1999; 11:1245–50). This infection is sometimes associated with an autoimmune reaction leading to atrophy of the corpus mucosa (Ozasa, K., et al., Dig Dis Sci 1999; 44: 253–6). A common feature of gastric autoimmunity and frequently several other autoimmune diseases, e.g., thyroiditis, insulin dependent diabetes mellitus and sometimes rheumatoid arthritis, is the occurrence of parietal cell autoantibodies (Bech, K., et al., Acta Endocrinol 1991, 124: 534–9; Barrio, R., et al., Pediatr Endocrinol Metab 1997, 10: 511–6; Datta, A., et al., Indian J Med Res 1990, 92: 228–32; Mårdh, S., et al., Scand J Gastroenterol 1991, 26: 1089–96). The parietal cell H,K-ATPase $\Delta$- and $\beta$-subunits were found to be the major autoantigens in autoimmune atrophic gastritis (Karlsson, A., et al., J Clin Invest 1988, 81: 475–9; Song, Y. H., et al., Scand J Gastroenterol 1994, 29:122–7; Ma, J. Y., et al., Scand J Gastroenterol 1994, 20: 790–4). A low titre of H,K-ATPase antibodies is normally found in healthy individuals due to the normal turn-over of parietal cells. In patients with inflamed corpus mucosa the titre may be increased.

Pepsinogen I (PGI) is secreted by the chief and mucous neck cells of the corpus mucosa into the lumen of the stomach but a small fraction (about 1%) leaks into the blood stream (Baron, J. H., Clinical tests of gastric secretion: History, Methodology and Interpretation. (1978) London: Macmillan). Increased serum concentrations of PGI are frequently found in patients with duodenal ulcer (Samloff, I. M., et al., Gastroenterol 1975 July, 69(1): 83–90). In patients with pernicious anaemia due to severe atrophy of the corpus mucosa serum PGI is significantly reduced (Samloff, I. M., et al., Gastroenterol 1982 July, 83(1 Pt 2): 204–9).

Existing, non-invasive methods of detecting gastrointestinal disorders include monitoring blood flow to the affected region to detect inflammation (U.S. Pat. No. 5,524,622). A significant disadvantage of this method is the requirement of injecting multiple substances into the patient followed by the detection by gamma camera. Additionally, the method only detects inflammation, and does not address the underlying cause of any inflammation. Other methods of detecting gastrointestinal disorders include assays for individual analytes such as pepsinogen (U.S. Pat. No. 5,879,897) or Helicobacter pylori (U.S. Pat. Nos. 5,814,455; 6,067,989; 6,068,985; 6,090,611). Other serological markers are gastrin (Borch, K., et al., Scand J Gastroenterol 1997, 32:198–202), pepsinogen II (Carmel, R., Am J Pathol 1998, 90: 442–5), intrinsic factor antibodies (Waters, H. M., et al., J Clin Pathol 1989, 42: 307–12) and pepsinogen antibodies (Mårdh, S., et al., Acta Physiol Scand 1989, 136: 581–7).

Although each one of these markers may be used to diagnose changes in the gastric mucosa, the overlap between healthy subjects and patients is great, and even greater among the various subgroups of patients. Therefore none of all these markers alone is sufficient for a reliable diagnosis.

SUMMARY OF THE INVENTION

The instant invention provides a screening method for gastritis in its various forms involving the evaluation of assay results for H,K-ATPase antibodies, *H. pylori* antibodies, and serum pepsinogen I concentration. The analysis of multiple analytes associated with gastritis provides a reliable indication of various subgroups of gastritis.

In one embodiment, the invention comprises a method for evaluating a blood sample from a patient to assess the likelihood that the patient has gastritis. In this method, the blood sample is tested for the presence of antibodies specific for H,K-ATPase, antibodies specific for *Helicobacter pylori*, and for the concentration of pepsinogen I. The levels of these analytes are compared with levels from individuals without gastritis, and the presence of H,K-ATPase antibodies, *Helicobacter pylori* antibodies or altered pepsinogen concentration is indicative of the patient having gastritis.

In another embodiment, the screening method for gastritis comprises determining H,K-ATPase antibodies, *Helicobacter pylori* antibodies, and the level of pepsinogen I in a biological sample from a patient suspected of suffering from gastritis, and comparing the level of the analytes to levels in normal individuals of the same species. Altered levels in the sample compared to the level in normal individuals of the same species is indicative of gastritis.

In a further embodiment, the screening method for gastritis comprises determining the levels of at least two indicators in a biological sample from a mammalian patient, the indicators selected from the group consisting of H,K-ATPase antibodies, *Helicobacter pylori* antibodies, and the level of pepsinogen I. The levels of indicators are compared to levels in normal mammals of the same species, and levels of at least two indicators in the sample which differ significantly from the level in normal mammals of the same species is indicative of gastritis. Determining the levels of the indicators may be achieved by immunoassays.

In a further embodiment of the invention, the screening method includes an additional indicator comprising the level of pepsinogen I multiplied by the level of *Helicobacter pylori* antibodies, which is also compared to the same indicator in normal mammals of the same species.

In another embodiment, the invention comprises a method of determining which one out of several subgroups of gastritis a patient has. H,K-ATPase antibodies, *Helicobacter pylori* antibodies, and the level of pepsinogen I, and the product of the level of pepsinogen I multiplied by the level of *Helicobacter pylori* antibodies are measured, and the results are compared to a flow-chart which shows various levels of the different analytes and which subgroup of gastritis is associated with them.

In an additional embodiment of the invention, a kit is provided for performing the screening method. The kit preferably comprises reagents suitable for detecting H,K-ATPase antibodies, *Helicobacter pylori* antibodies, and the level of pepsinogen I. The reagents for each of the three assays are preferably present in amounts to perform equal numbers of the three assays. Preferably, the method of detection is immunoassay, and the reagents include pepsinogen I antibodies, H,K-ATPase and *Helicobacter pylori* proteins, or peptides thereof.

DETAILED DESCRIPTION OF THE INVENTION

Gastritis and dyspepsia are common entities in primary health care but with poorly defined management. The aim of the present invention is to provide a serologic screening test for gastritis. Esophagogastroduodenoscopy (EGD) with biopsy and histological examination requires a skillful and experienced staff and it is presently the only reliable technique for diagnosing gastritis, benign ulcer and neoplasia. The last two groups are generally closely associated with chronic gastritis. Previous investigations often concluded that serology has a limited diagnostic value. However, the instant evaluation scheme for analyzing serology data is useful as a pregastroscopic screening of dyspepsia, irrespective of the age of the patient, which is a remarkable improvement compared with previous reports (Bodger, K., et al., Scand J Gastroenterol 1999, 34: 856–63; Moayyedi, P., et al., Eur J Gastroenterol Hepatol 1999, 11:1245–50). The immune system and chemical signalling from the inflamed gastric mucosa provide serum analytes and diagnostic possibilities for detection of gastritis.

Assay methods for determining the level of H,K-ATPase antibodies, *Helicobacter pylori* antibodies and pepsinogen I concentration are known. In a preferred embodiment of the instant invention, the method of determining the level of the analytes is by immunoassay. The immunoassay may be any of the well-known methods, including, but not limited to, enzyme-linked-immunosorbent assays (ELISA), enzyme immunoassay (EIA), radioimmunoassay (RIA), immuno-precipitation (IP), and optical or electrochemical detection of immuno-ligand interaction. In a preferred embodiment, the immunoassay is one in which the antigen is immobilized on a solid support, sample is added, followed by labelled antibody.

One embodiment of the invention is a kit for screening for gastritis. The kit comprises the reagents required to perform assays for at least two indicators selected from the group consisting of H,K-ATPase antibodies, *Helicobacter pylori* antibodies, and the level of pepsinogen I. In a preferred embodiment, the assays are immunoassays, and the kit comprises analytes immobilized on one or more solid supports, such as a microtitre plate, strip of paper, nitrocellulose or other suitable material. Labeled antibody is included for detection. The kit preferably contains reagents for each assay in amounts sufficient to perform equal numbers of the different assays. For example, a kit may contain sufficient reagents to perform ten H,K-ATPase assays, ten *Helicobacter pylori* assays and ten pepsinogen assays. The kit may additionally comprise analyte-specific antibodies, labelling reagents, positive and negative controls and wash solutions.

The immunoassay methods are based on analyses of a blood sample (or plasma or serum) from patients; the autoantibodies against H,K-ATPase, antibodies against *Helicobacter pylori* and concentration of pepsinogen are assayed. All of these analytes serve as markers of an inflammatory condition in the gastric mucosa. The methods of detecting the analytes, such as immunoassays, are well-known in the art.

The assay results are analysed by a new grouping procedure in which the results are compared with reference values from healthy individuals from the normal population. A mathematical expression (the product of pepsinogen concentration multiplied by the titre of *Helicobacter pylori* antibodies) is essential to identify one particular group of patients. Other mathematical procedures may be used provided they achieve determination of a useful grouping of gastritis patients. This grouping procedure diagnoses inflammatory conditions in the gastric mucosa that previously have required the more costly and complicated gastroscopy with histopathological examination of biopsies from the mucosa.

The reference values from healthy individuals from the normal population may be standardized for each assay. In this embodiment, the test results are compared to standardized reference values in order to determine the patient's likelihood of having gastritis. A kit would contain a list of the standardized reference values for each assay. In an alternative embodiment, the reference values are obtained by testing a normal control along with the patient samples. In this embodiment, a kit would contain a normal control and standards. When performing the assays, one would run the assay on the control and standards at the same time the patient samples are tested. The assay results for the control and standards would then be compared to the results for the patient samples.

Sera from subjects examined with gastroscopy and biopsy were analysed for H,K-ATPase antibodies, *Helicobacter pylori* antibodies, and pepsinogen I. The diagnoses were normal gastric mucosa (n=50), duodenal ulcer (n=53), and atrophic corpus gastritis with (n=50) or without pernicious anaemia (n=46). An evaluation scheme (flow chart) was constructed to optimise the diagnostic agreement between serology and gastric mucosal morphology. Four major serologic groups and thirteen subgroups were obtained with an over-all sensitivity to detect gastritis of 98% (146/149) (95% CI 94–100%) and a specificity of 84% (42/50) (95% CI 71≅93%). Additional sera from 483 subjects from the general population were grouped by serology. The overall sensitivity to detect gastritis in this population was 88% (211/240) (95% CI 83–92%) with a specificity of 81% (196/243) (95% CI 75–85%). There was a good agreement between serology and the gastric mucosal morphology both in the groups used for developing the evaluation scheme and in the sample of the general population. Thus, serology is appropriate for initial identification of subjects with a normal gastric mucosa, those who qualify for eradication of *Helicobacter pylori*, and those who are at risk of developing malignancy and therefore require gastroscopic examination.

In reading the assay results, altered levels of the analytes in a patient sample as compared to normal control values is indicative of the patient having gastritis. By "altered" is meant levels either significantly above or significantly below the levels of the normal control. What is significant depends on the accuracy and precision of the specific test performed and may be determined empirically without undue experimentation. Additionally, the levels of multiple analytes in a patient sample are compared to normal control values in order to obtain a more accurate determination of whether or not the patient has gastritis. For example, in general, patient levels of H,K-ATPase antibodies and *Helicobacter pylori* antibodies above normal control levels is indicative of gastritis, while patient levels of the pepsinogen concentration either significantly above (duodenal ulcer) or below (severe atrophy of the corpus mucosa) normal control levels may be indicative of gastritis. The pepsinogen concentration multiplied by the *Helicobacter pylori* antibody titre either significantly above or significantly below the normal control may be indicative of gastritis. In order to determine the likelihood of the patient having gastritis and/or to determine the subgroup of the patient's gastritis, the combination of multiple assay results are compared to normal control values. Because some analytes may be either higher or lower than normal control levels and still be indicative of gastritis, the comparison of levels of multiple analytes in a patient sample to normal control levels of the same analytes provides a more accurate determination of gastritis.

Figure 2:
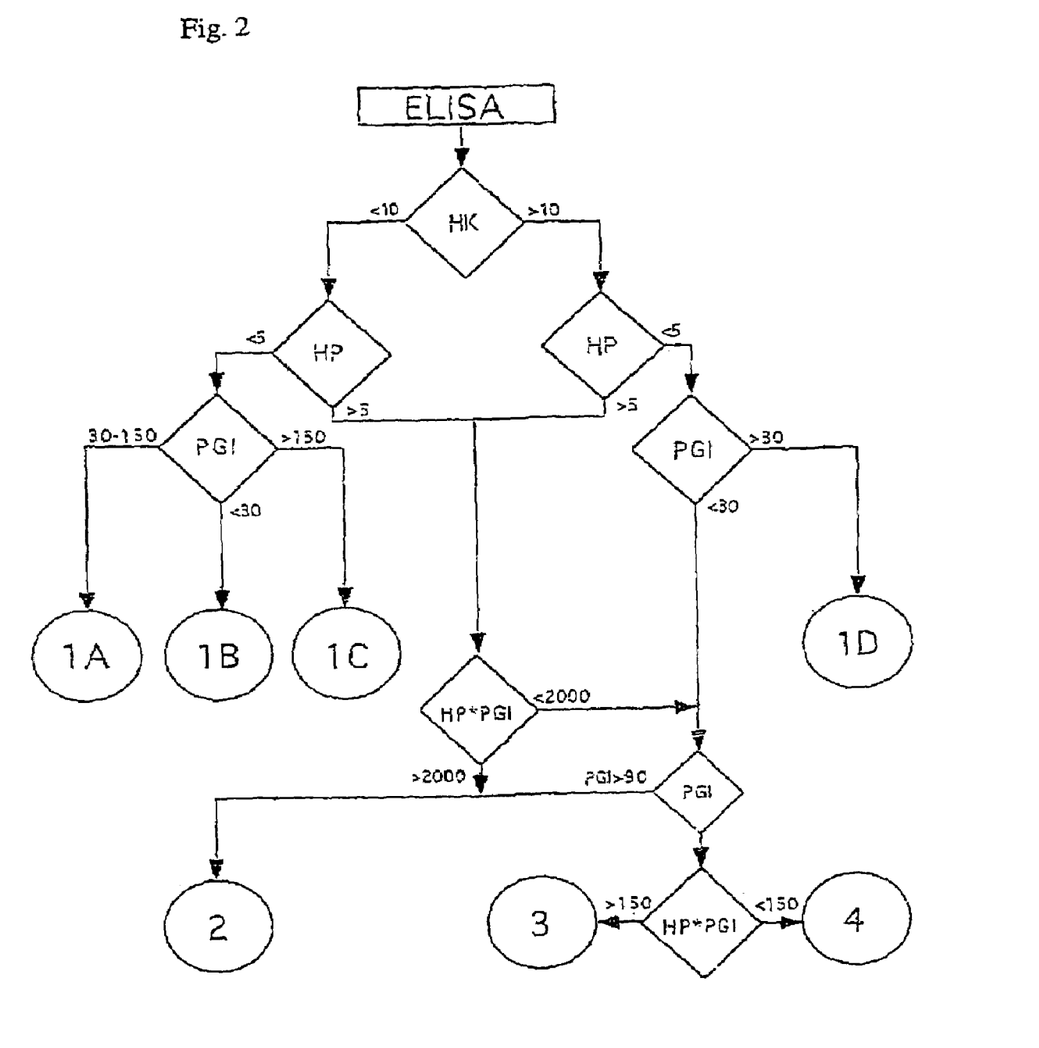
FIG. 2 is a flow chart-depicting a testing evaluation scheme.
Figure 3A:
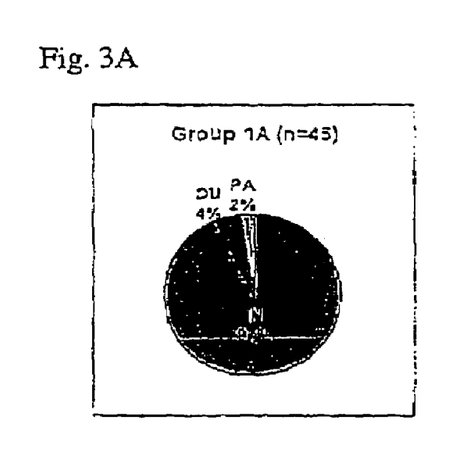
FIGS. 3A–3D are pie charts showing the four major groups identified by the screening tests of the instant invention for the test groups N, DU, AG, and PA.
Figure 3B:
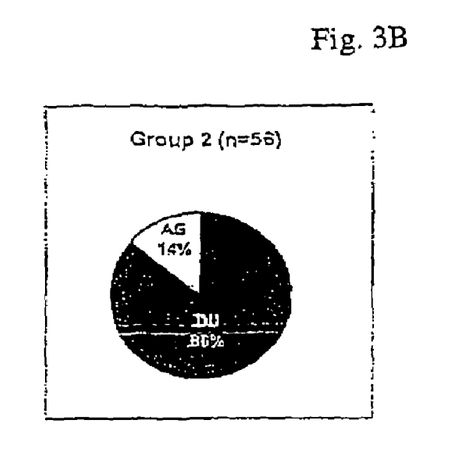
Figure 3C:
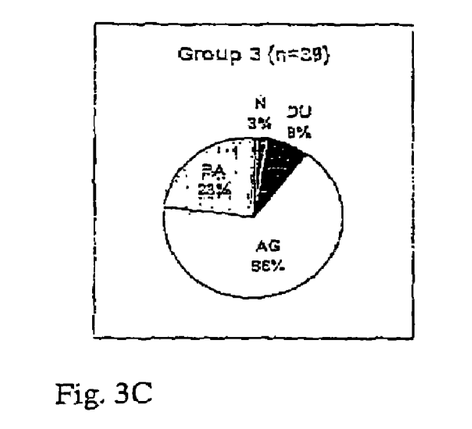
Figure 3D:
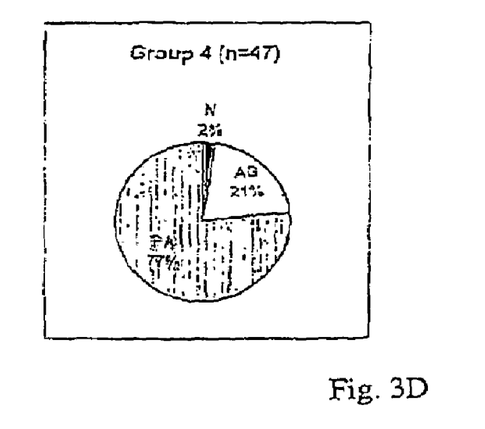
Figure 4A:
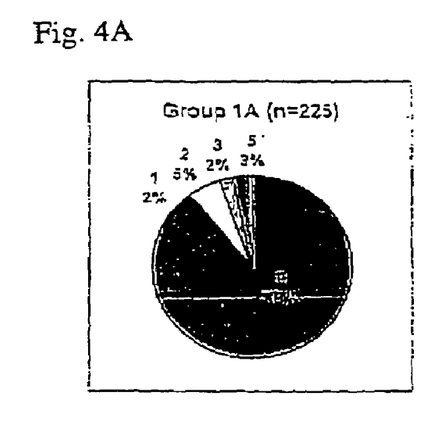
FIGS. 4A–4D are pie charts showing the four major groups identified by the screening tests of the instant invention for the general population.
Figure 4B:
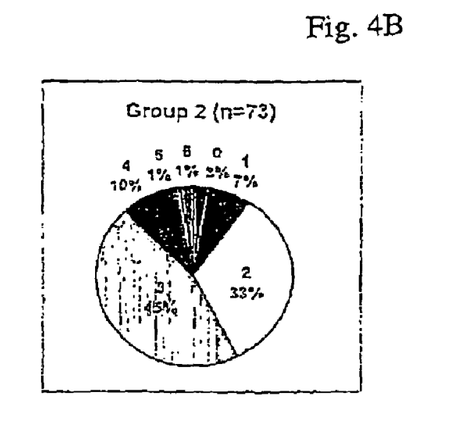
Figure 4C:
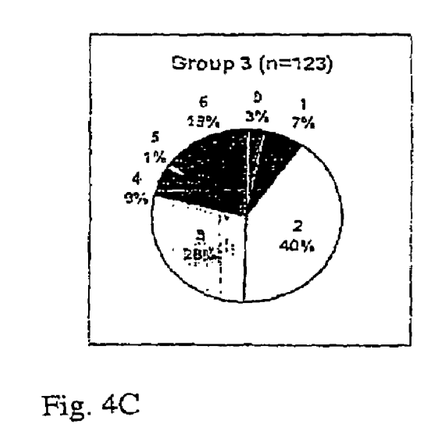
Figure 4D:
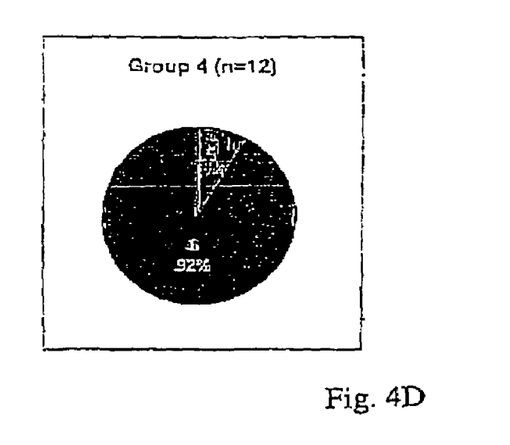

With histomorphological examination as the gold standard, the present invention demonstrates that a combination of serologic assays detects 87% (196/225, group 1A in FIG. 2; Table 2) of subjects with normal gastric mucosa in a sample of the general population and in the study groups it was 84% (42/50, group 1A; Table 1). In the study groups, serology detected 91% (48/53, group 2) of subjects with duodenal ulcer and 84% (81/96, groups 3 plus 4) of subjects with corpus predominant atrophic gastritis with or without pernicious anaemia. All subjects with pernicious anaemia were obtained in group 4. In the population sample, groups 2A–D comprised 15%. Among these, only 3% had a normal mucosa, while antral gastritis with atrophy and pangastritis overall comprised 88%. All subjects in groups 2A–D were *H. pylori*-positive. It is therefore suggested that subjects aged 40–50 years or less (Bodger, K., et al., Scand J Gastroenterol 1999, 34: 856–63; Moayyedi, P., et al., Eur J Gastroenterol Hepatol 1999, 11:1245–50) that are obtained in groups 2A–D may be treated according to the current recommendations for peptic ulcer disease.

Only 12 subjects in the population sample were obtained in group 4A–4C; one had non-atrophic corpus predominant gastritis and the remaining 11 atrophic corpus predominant gastritis. Thus, subjects belonging to group 4 should be recommended EGD due to the increased risk of malignancy.

In the population sample there were 12% (29/225) with normal gastric mucosa, but abnormal results of the serological analysis. There are probably several explanations for this discrepancy; some results of serum analytes may reflect a previous inflammatory condition, or the ELISAs may be more sensitive than the most experienced examiner to detect small changes in the mucosa.

In conclusion, EGD with biopsy remains the gold standard for an accurate diagnosis of the status of the gastric mucosa. However, as the following examples show, serology is a good complement when combined with the patient's symptomatology and medical history. It functions as a "serologic biopsy". Therefore, serologic assays are well-suited for pregastroscopic screening of dyspepsia to identify: (a) patients with normal gastric mucosa (group 1A), (b) *H. pylori*-positive patients with high levels of serum PGI and high "H.p.×PGI-factor" (group 2), and (c) patients with corpus predominant atrophic gastritis (groups 3 plus 4). Patients in (a) may be examined further for "non-acid-related" disorders, those in (b) younger than 40–50 years may be treated according to the recommendations for peptic ulcer disease, and in cases with unsuccessful treatment, the patients should be referred to EGD. Patients in (c) are at a higher risk of developing gastric malignancy and should therefore be referred to EGD.

The described serologic assays and the evaluation procedure are simple and may be performed in any clinical laboratory with some experience in immunoassays. They provide a reduction in the endoscopic workload, are beneficial for the patient, provide a valuable diagnostic tool for the doctor and are cost-efficient.

EXAMPLE 1

For the initial evaluation of the serologic results, sera from four groups of subjects examined endoscopically and histologically were selected; 50 subjects with normal gastric mucosa (N) (38 males and 12 females, median age 63 years, range 37–80), 53 subjects with acute duodenal ulcer (DU) (39 males and 14 females, median age 52 years, range 20–79), 46 subjects diagnosed as having mild to severe corpus predominant atrophic gastritis (AG) (23 males and 23 females, median age 68 years, range 40–82), and 50 subjects with corpus predominant atrophic gastritis with pernicious anaemia (PA) (23 males and 27 females, median age 68 years, range 40–83). The criteria for the diagnosis of pernicious anaemia which included a Schilling test showing intrinsic factor deficiency have previously been given (Borch, K., et al., Scand J Gastroenterol 1984, 19: 154–60).

EXAMPLE 2

A sample of 483 subjects (266 males and 217 females, median age 65, range 37 to 85 years) randomly selected from a general population in Sweden was examined with EGD with biopsy and blood sampling. Results of this study have recently been published (Borch, K., et al., Dig Dis Sci, 2000, 45: 1322–29). In biopsy specimens, gastritis was classified according to the Sydney system into antrum predominant-, corpus predominant- and pangastritis with or without atrophy and with or without presence of *H. pylori* (Price, A., J Gastroenterol Hepatol 1991, 6: 209–22; Dixon, M. F., et al., Am J Surg Pathol 1996, 20: 1161–81). EGD was performed as previously described (Borch, K., et al., Dig Dis Sci, 2000, 45: 1322–29). Three biopsies were taken from the gastric body (major-, anterior-, and posterior aspect), and the antrum within 3 cm of the pylorus.

EXAMPLE 3

Preparation of Antigens

H,K-ATPase was prepared from pig gastric mucosa as previously described (Mårdh, S., et al., Scand J Gastroenterol 1991, 26: 1089–96). The binding of autoantibodies against the H,K-ATPase in this porcine antigen preparation was similar to that of the human antigen (Song, Y. H., et al., Scand J Gastroenterol 1994, 29: 122–7; Ma, J. Y., et al., Scand J Gastroenterol 1994, 20: 790–4; Karlsson, F. A., et al., Clin exp Immunol 1987, 70:604–10). The vesicular membranes enriched with H,K-ATPase were treated at a low concentration of detergent (0.13% (w/v) of n-octylglucoside, or 0.06% (w/v) of sodium dodecylsulfate) to remove loosely attached proteins, e.g., pepsin/pepsinogen, and then stored at −70° C. in sucrose/Hepes-Tris buffer, pH 7.4. Antigens of *H. pylori* were prepared from five strains (CCUG 17874, 25, 66, 1139 and 253) as described by Ma et al. (Ma, J. Y., et al., Scand J Gastroenterol 1994, 29: 961–6).

EXAMPLE 4

Enzyme-Linked Immunosorbent Assay (ELISA)

ELISA was performed essentially as described (Ma, J. Y., et al., Scand J Gastroenterol 1994, 29: 961–6) using Nunc-Immuno® plates (Maxisorp®, Nunc, Roskilde, Denmark) coated with 50 µl of indicated antigen preparations (5 µg/ml) in 50 mM sodium carbonate buffer, pH 9.8, and incubated overnight at 4° C. The wells were sequentially incubated with sera diluted 1:100 in phosphate-buffered saline containing 0.05% (v/v) Tween 20 (PBS-T), biotinylated goat anti-human IgG (Amersham International PLC, Amersham, UK), streptavidin (Amersham International PLC, Amersham, UK), and biotinylated alkaline phosphatase (Boehringer-Mannheim Biochemicals, Mannheim, Germany). Finally, 100 µl of p-nitrophenyl phosphate (Sigma, St Louis, Mo., USA) at 1 mg/ml in 50 mM sodium carbonate buffer, pH 9.8, was added. The absorbance was read continuously at 405 nm (kinetic ELISA) using a computerized ELISA reader (Vmax®, Molecular Devices, CA, USA). All incubations were performed with continuous shaking and the plates were washed three times with PBS-T between each incubation step. Each serum sample was analyzed in duplicates, and in each immuno plate positive and negative standards were included. The reading of the optical density (mOD per min) for each sample was related to the positive standard on each immuno plate, and the data are presented as relative titres of antibody. The coefficient of variation of the positive and negative standards were 5.7±2.9 and 8.1±3.5 (M+SD), respectively.

EXAMPLE 5

Analysis of Serum Pepsinogen I (PGI)

The assay was based on a noncompetitive sandwich technique using a horseradish peroxidase (HRP)-labeled antibody specific for PGI to detect PGI bound to a stationary antibody. The latter antibody was immobilized on a microtitre plate and had affinity for a different antigenic site in PGI than the enzyme-labeled antibody.

Assay of serum pepsinogen I (PGI) was carried out using Gastroset PGI (Gastroset PGI Cat. No. 67882, Orion Diagnostica, Espoo, Finland) according to the manufacturer's instructions. Aliquots of 20 µL of standards, control and serum sample were added in duplicate into microtitre wells precoated with stationary pepsinogen I antibody. Assay buffer (100 µL) was added and the microtitre wells incubated for 30 minutes, washed twice, and then incubated for another 30 minutes with horseradish peroxidase-labeled PGI (HRP-PGI) antibody diluted 1:100 with assay buffer. The wells were washed four times and then incubated with substrate solution for 30 minutes; the reaction was stopped and color development measured in an ELISA-reader.

Statistical Analysis

Results are presented as median and interquartile range (25th–75th percentiles). Proportions (percentages) are given with 95 percent confidence interval (CI), when considered relevant. Wilcoxon's signed-rank test was used to evaluate differences between pairs of patient groups. The level of significance was $p<0.05$.

EXAMPLE 6

Assays of Sera from the Study Groups N, DU, AG and PA

Figure 1A:
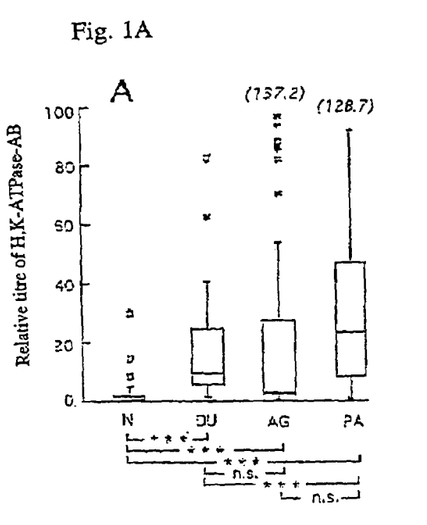
FIGS. 1A–1D are graphs showing the levels of H,K-ATPase antibodies, *H. pylori* antibodies, pepsinogen I, and result of *H. pylori* antibody level multiplied by pepsinogen I concentration, respectively, for individuals with normal gastric mucosa (N) and those with duodenal ulcer (DU), atrophic gastritis (AG) and gastritis with pernicious anemia (PA).
Figure 1B:
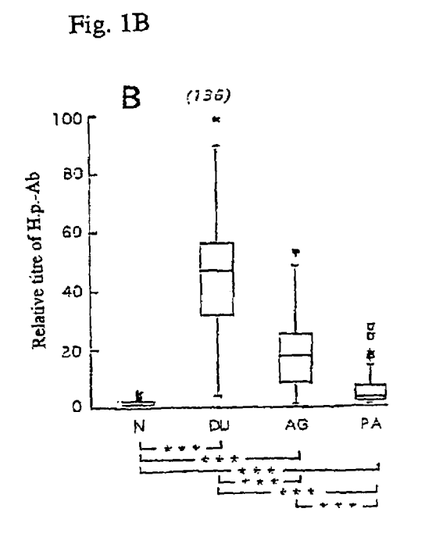
Figure 1C:
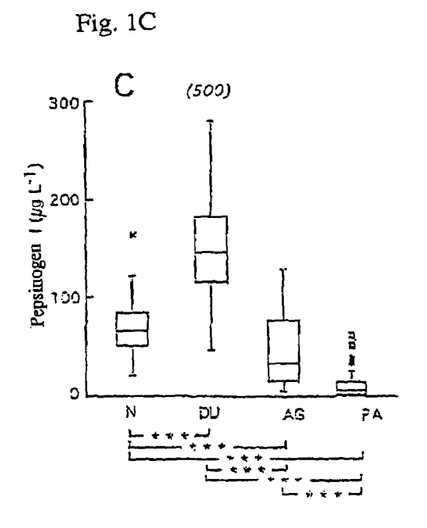

Enzyme-linked immunosorbent assay—Sera of four groups of subjects that had their diagnosis at endoscopy and histological examination of biopsies were analyzed for H, K-ATPase antibodies (FIG. 1A), *H. pylori* antibodies (FIG. 1B), and pepsinogen (PGI) (FIG. 1C). The product f=[relative titre of *H. pylori* antibodies×PGI] is presented in FIG. 1D. The groups included subjects with a normal gastric mucosa (N, n=50), duodenal ulcer (DU, n=53), mild to severe corpus predominant atrophic gastritis (AG, n=46), and pernicious anaemia (PA, n=50). The results are presented as box plots with median and interquartile range (25th–75th percentiles, Hspread). Values outside the inner and outer fences are plotted with asterisks and open circles, respectively, and the upper fences are defined as the interquartile range+1.5 Hspread and +3 Hspread, respectively (SYSTAT® manual). Values outside the y-axis are presented in parenthesis. Significance is denoted by  ($p<0.01$) and * ($p<0.001$); n.s. not significant.

H,K-ATPase antibodies—In the study group constituting subjects with normal gastric mucosa (N), the median H,K-ATPase antibody titre was 2.0 (range 0.7–9.0; FIG. 1A). Corresponding values in the DU, AG, and PA groups were 9.3 (range 1.6–82.7), 3.8 (range 0.8–137) and 32.3 (range 1.4–128), respectively ($p<0.001$ vs. normals).

*Helicobacter pylori* antibodies—The median titre of *H. pylori* antibodies in group N was 1.0 (range 1.0–4.5; FIG. 1B). Corresponding values in the DU, AG, and PA groups were 47.5 (range 4.1–136), 18.0 (range 1.0–53.0) and 3.5 (range 1.3–27.2), respectively ($p<0.001$ vs. normals).

Serum pepsinogen I—The median value of serum PGI in group N was 66.3 μg per L (range 21.3–163; FIG. 1C). Corresponding values in the DU, AG, and PA groups were 149 μg per L (range 47.2–500), 31.8 μg per L (range 2.6–127), and 4.4 μg per L (range 0–61.0), respectively ($p<0.001$ vs. normals).

Figure 1D:
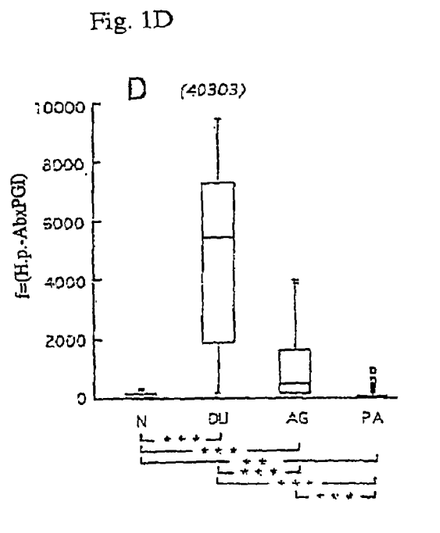

The factor f=(titre of *H. pylori* antibodies×serum pepsinogen I). Although the patient groups differed significantly using the three types of serologic parameters, there was an overlap. The titres of *H. pylori* antibodies and the PGI concentrations were high in the DU group and low in the PA group. Therefore, in an attempt to distinguish better between the different groups, the products (f) of the analytical results from the ELISAs of *H. pylori* antibodies times the PGI were evaluated (FIG. 1D). All groups were significantly different from the others ($p<0.01$ or $p<0.001$, FIG. 1D). The median value of f in group N was 77.5 (range 24.0–344). In the DU group it was 8105 (range 193–40303; $p<0.001$ vs. normals), in AG 500 (range 5.0–3901; $p<0.001$ vs. normals), and in PA 12.0 (range 0–915; $p<0.01$ vs. normals).

EXAMPLE 7

Evaluation Scheme (Flow Chart) for Serologic Diagnosis

The status of the gastric mucosa was determined by means of histopathological examination of biopsy sections. This made possible a comparison of the gold standard with the results of serologic analyses. A diagnostic evaluation scheme was developed (FIG. 2). The discriminating levels of this scheme were optimized using the results of the serologic analyses (after omitting serologic outliers) in the study groups N, DU, AG and PA. The SYSTAT® software was used to achieve a maximal resolution between the patient groups. The "analytes" were H, K-ATPase antibodies (HK), *H. pylori* antibodies (HP), s-pepsinogen I (PGI), and f=(titre of *H. Pylori* antibodies×serum pepsinogen I) (HP*PGI). This scheme sorted the individual sera into the serologic groups 1–4 and their subgroups.

The evaluation scheme was applied to the analytical results from each individual serum which was sorted and grouped accordingly. Table 1 shows the serologic grouping of the four study groups: normal (N), duodenal ulcer (DU), corpus predominant gastritis without pernicious anaemia (AG) and pernicious anaemia (PA). The scheme for serologic diagnosis given in FIG. 2 was applied to the serological data.

The grouping resulted in the serologic subgroups 1A–4C. The discriminating levels are indicated for the selection pathway in each subgroup and the median value of each group is indicated in parenthesis. The distribution of the study groups, sex and age in each serologic group are presented. In group 1A, 84% (42/50) of the subjects in group N were obtained. Some sera from subjects in group N were serological outliers (e.g., in groups 1B–1D, 3A and 4A). In the groups 2A–2D, 91% (48/53) of subjects with DU were obtained. In groups 3A and 3B, 57% (26/46) of those with AG and 18% (9/50) of those diagnosed with PA were obtained. In groups 4A–4C, 72% (36/50) of those with PA and 22% (10/46) of those with AG were obtained. This overlap between the AG and PA group is not surprising since they represent the same disease, but on a different point of the time scale. Furthermore, an individual overlap was indicated by the 14% of the subjects with AG found in group 2. Otherwise the overlaps appeared small. The overall sensitivity to detect gastritis was 98% (146/149) (95% CI 94–100%) and the specificity 84% (42/50) (95% CI 71–93%).

TABLE 1

| Serological Group | 1A | 1B | 1C | 1D | 2A | 2B |
|---|---|---|---|---|---|---|
| | | | Selection Pathway | | | |
| HK | <10 (2.0) | <10 (2.6) | <10 (1.0) | >10 (24.0) | <10 (4.2) | <10 (7.1) |
| HP | <5 (1.0) | <5 (2.0) | <5 (1.0) | <5 (2.0) | >5 (46.0) | >5 (10.0) |
| PGI | 30–150 (70) | <30 (17) | >150 (163) | >30 (43) | —136 | —122 |
| HP*PGI | —83 | —20 | —163 | —129 | >2000 (6755) | <2000 (1216) |
| PGI | — | — | — | — | — | >90 |
| HP*PGI | — | — | — | — | — | — |
| | | | Clinical Groups | | | |
| n = 199 | 45 | 7 | 1 | 4 | 30 | 2 |
| Normal (50) | 42 | 3 | 1 | 2 | 0 | 0 |
| DU (53) | 2 | 0 | 0 | 0 | 23 | 2 |

TABLE 1-continued

| | | | | | | |
|---|---|---|---|---|---|---|
| AG (46) | 0 | 1 | 0 | 1 | 7 | 0 |
| PA (50) | 1 | 3 | 0 | 1 | 0 | 0 |
| Sex | | | | | | |
| M 123 (62%) | 35 (77.8%) | 4 (57.1%) | 1 | 2 (50%) | 21 (70%) | 1 (50%) |
| F 76 (38%) | 10 (22.2%) | 3 (42.9%) | — | 2 (50%) | 9 (30%) | 1 (50%) |
| Age | | | | | | |
| median 67 | 66 | 60 | 71 | 69 | 59 | 43 |
| range 20–83 | 37–80 | 38–75 | — | 61–78 | 20–79 | 38/48 |

| Serological Group | 2C | 2D | 3A | 3B | 4A | 4B | 4C |
|---|---|---|---|---|---|---|---|
| Selection Pathway | | | | | | | |
| HK | >10 (25.0) | >10 (10.3) | <10 (2.0) | >10 (42.0) | <10 (2.3) | >10 (67.0) | >10 (39.0) |
| HP | >5 (53.5) | >5 (11.4) | >5 (18.5) | >5 (17.0) | >5 (7.0) | >5 (6.0) | <5 (2.0) |
| PGI | –150 | –148 | –36 | –23 | –9 | –4 | <30 (8) |
| HP*PGI | >2000 (9232) | <2000 (1602) | <2000 (673) | <2000 (425) | <2000 (79) | <2000 (28) | <150 (8) |
| PGI | — | >90 | <90 | <90 | <90 | <90 | — |
| HP*PGI | — | — | >150 | >150 | <150 | <150 | — |
| Clinical Groups | | | | | | | |
| n = 199 | 22 | 2 | 24 | 15 | 5 | 11 | 31 |
| Normal (50) | 0 | 0 | 1 | 0 | 1 | 0 | 0 |
| DU (53) | 21 | 2 | 1 | 2 | 0 | 0 | 0 |
| AG (46) | 1 | 0 | 17 | 9 | 2 | 3 | 5 |
| PA (50) | 0 | 0 | 5 | 4 | 2 | 8 | 26 |
| Sex | | | | | | | |
| M 123 (62%) | 18 (81.8%) | 1 (50%) | 12 (50%) | 6 (40%) | 3 (60%) | 5 (45.5%) | 14 (45.2%) |
| F 76 (38%) | 4 (18.2%) | 1 (50%) | 12 (50%) | 9 (60%) | 2 (40%) | 6 (54.5%) | 17 (54.8%) |
| Age | | | | | | | |
| median 67 | 53 | 58 | 70 | 68 | 72 | 73 | 70 |
| range 20–83 | 23–79 | 48–68 | 40–83 | 34–82 | 54–82 | 54–82 | 44–81 |

FIGS. 3A–3D present the distribution profiles of the four major histomorphologically diagnosed groups identified by serology: group 1A, comprising 94% N, 4% DU and 2% PA; group 2 (A–D) comprising 86% DU and 14% AG; group 3 (A–B) comprising 66% AG, 23% PA, 8% DU, and 3% N; and group 4(A–C) comprising 77% PA, 21% AG, and 2% N. Together groups 3 and 4 comprised 95% of subjects in groups AG and PA (42% and 53%, respectively), 2% N, and 3% DU. A smaller group represented by groups 1B–D in Table 1, comprised twelve subjects of whom 50% belonged to group N, but serologically they were outliers. The remaining six subjects in these subgroups had either AG (17%) or PA (33%).

EXAMPLE 8

Serologic Diagnosis in a Sample of the General Population

A sample of 483 subjects (age 37 to 85 years) randomly selected from a general population in Sweden was previously examined with EGD with biopsy and blood sampling. Fifty percent (243/483) had a normal gastric mucosa and the remaining had gastritis (Borch, K., et al., Dig Dis Sci, 2000, 45: 1322–29). In the present study sera from this population were analysed and grouped according to the scheme in FIG. 2 and the outcome compared with that of the histomorphological diagnosis. Table 2 shows the serologic grouping of the general population sample. The scheme for serologic diagnosis given in FIG. 2 was applied to the serologic data. The grouping resulted in the serologic subgroups 1A–4C. The discriminating levels are indicated for the selection pathway in each subgroup and the median value of each group is indicated in parenthesis. The distributions of the histomorphologically diagnosed groups, sex, and age in each serologic subgroup are presented. The morphological diagnose were normal (0), non-atrophic antrum predominant gastritis (1), atrophic antrum predominant gastritis (2), non-atrophic pangastritis (3), atrophic pangastritis (4), non-atrophic corpus predominant gastritis (5), and atrophic corpus predominant gastritis (6).

TABLE 2

| Serological Group | 1A | 1B | 1C | 1D | 2A | 2B |
|---|---|---|---|---|---|---|
| Selection Pathway | | | | | | |
| HK | <10 (1.8) | <10 (1.5) | <10 (1.6) | >10 (17.8) | <10 (2.6) | <10 (2.3) |
| HP | <5 (0.9) | <5 (1.1) | <5 (1.2) | <5 (1.1) | >5 (30.3) | >5 (11.2) |
| PGI | 30–150 (63) | <30 (22) | >150 (227) | >30 (64) | –96 | –107 |
| HP*PGI | –56 | –22 | –248 | –60 | >2000 (2691) | <2000 (1189) |

TABLE 2-continued

| Serological Group | 1A | 1B | 1C | 1D | 2A | 2B |
|---|---|---|---|---|---|---|
| PGI | — | — | — | — | — | >90 |
| HP*PGI | — | — | — | — | — | — |

Histomorphological Diagnosis

| | | | | | | |
|---|---|---|---|---|---|---|
| n = 483 | 225 | 18 | 7 | 25 | 38 | 22 |
| 0 (normal) 243 (50.3%) | 196 | 16 | 5 | 20 | — | 2 |
| 1 (ant) 20 (4.1%) | 5 | — | 1 | 1 | 3 | 1 |
| 2 (ant a) 87 (18.1%) | 12 | — | 1 | — | 14 | 5 |
| 3 (pan) 74 (15.3%) | 5 | — | — | 1 | 14 | 13 |
| 4 (pan a) 14 (2.9%) | 0 | — | — | — | 6 | — |
| 5 (corp) 13 (2.7%) | 7 | 1 | — | 2 | — | 1 |
| 6 (corp a) 32 (6.6%) | 0 | 1 | — | 1 | 1 | — |

Sex

| | | | | | | |
|---|---|---|---|---|---|---|
| M 261 (54%) | 127 (56.4%) | 7 (38.9%) | 6 (85.7%) | 11 (44.0%) | 23 (60.5%) | 16 (72.2%) |
| F 222 (46%) | 98 (43.6%) | 11 (61.1%) | 1 (14.3%) | 14 (56.0%) | 15 (39.5%) | 6 (27.3%) |

Age

| | | | | | | |
|---|---|---|---|---|---|---|
| median (65) | 56 | 52 | 66 | 62 | 65 | 63 |
| range (37–85) | 37–81 | 38–74 | 47–85 | 37–78 | 44–81 | 41–74 |

| Serological Group | 2C | 2D | 3A | 3B | 4A | 4B | 4C |
|---|---|---|---|---|---|---|---|

Selection Pathway

| | | | | | | | |
|---|---|---|---|---|---|---|---|
| HK | >10 (30.3) | >10 (69.4) | <10 (2.0) | >10 (31.1) | <10 (2.2) | >10 (70.5) | >10 (68.5) |
| HP | >5 (28.4) | >5 (12.2) | >5 (16.4) | >5 (18.8) | >5 (7.4) | >5 (7.3) | <5 (1.5) |
| PGI | −141 | −112 | −61 | −49 | −8 | −9 | <30 (8) |
| HP*PGI | >2000 (4140) | <2000 (1318) | <2000 (953) | <2000 (805) | <2000 (62) | <2000 (61) | <150 (18) |
| PGI | — | >90 | <90 | <90 | <90 | <90 | — |
| HP*PGI | — | — | >150 | >150 | <150 | <150 | — |

Histomorphological Diagnosis

| | | | | | | | |
|---|---|---|---|---|---|---|---|
| n = 483 | 10 | 3 | 95 | 28 | 2 | 4 | 6 |
| 0 (normal) 243 (50.3%) | — | — | 4 | — | — | — | — |
| 1 (ant) 20 (4.1%) | 1 | — | 8 | — | — | — | — |
| 2 (ant a) 87 (18.1%) | 3 | 2 | 39 | 11 | — | — | — |
| 3 (pan) 74 (15.3%) | 5 | 1 | 26 | 9 | — | — | — |
| 4 (pan a) 14 (2.9%) | 1 | — | 5 | 2 | — | — | — |
| 5 (corp) 13 (2.7%) | — | — | 1 | — | — | — | 1 |
| 6 (corp a) 32 (6.6%) | — | — | 12 | 6 | 2 | 4 | 5 |

Sex

| | | | | | | | |
|---|---|---|---|---|---|---|---|
| M 261 (54%) | 7 (70%) | 3 (100%) | 44 (46.3%) | 12 (43%) | 2 (100%) | 2 (50%) | 1 (17%) |
| F 222 (46%) | 3 (30%) | — | 51 (53.7%) | 16 (57%) | — | 2 (50%) | 5 (83%) |

Age

| | | | | | | | |
|---|---|---|---|---|---|---|---|
| mediam (65) | 63 | 67 | 63 | 68 | 75 | 76 | 72 |
| range (37–85) | 44–73 | 58–72 | 38–80 | 43–80 | 47–82 | 69–80 | 50–80 |

In group 1A, 87% (196/225) of the subjects exhibited serologic values indicating a normal gastric mucosa. Seven percent (16/243) of the subjects with normal gastric mucosa had low levels of PGI and were obtained in group 1B, while 8% (20/243) were obtained in group 1D due to increased levels of H,K-ATPase antibodies. Six percent (29/483) of the population sample diagnosed as having gastritis of any type were obtained in group 1A.

In groups 2A–2D, 15% (73/483) were obtained by means of the serologic grouping procedure (Table 2). In groups 2A–2D only two subjects had normal mucosa. The dominating morphological diagnoses in groups 2A–2D were antrum predominant gastritis with atrophy (24 subjects) and pangastritis without atrophy (33 subjects). Subjects in groups 3A–3B exhibited a positive serology for *H. pylori*. In group 3A, 20% (95/483) of the population were obtained and the dominating morphological diagnoses were antrum predominant gastritis with atrophy (39 subjects), pangastritis without atrophy (26 subjects), and pangastritis with atrophy or corpus predominant atrophic gastritis (17 subjects). In groups 4A–4C, the PGI values were generally low which indicated a more pronounced corpus atrophy. Only twelve subjects were found in these groups and they had corpus predominant gastritis with atrophy. The overall sensitivity to detect gastritis serologically in the population was 88% (211/240) (95% CI 83–92%) and the specificity 81% (196/243) (95% CI 75–85%).

The distribution profile according to serology in the four major groups of the sample of the general population is presented in FIGS. 4A–4D. The distribution profiles of the histomorphologically diagnosed groups in the serologic groups 1A, 2(A–D), 3(A–B) and 4(A–C) are presented. The morphological diagnoses were normal (O), non-atrophic antrum predominant gastritis (1), atrophic antrum predominant gastritis (2), non-atrophic pangastritis (3), atrophic pangastritis (4), non-atrophic corpus predominant gastritis (5), and atrophic corpus predominant gastritis (6).

In group 1A, the morphologically assessed normals comprised 87% (196/225). In group 2, antrum gastritis with atrophy, comprising 33% (24/73), and pangastritis, comprising 45% (33/73), were the dominating groups. In group 3 (A–B), antrum gastritis with atrophy, 40% (50/123), pangastritis, 28% (35/123), and atrophic corpus gastritis, 15% (18/123) were the dominating groups. In group 4 (A–C), atrophic corpus gastritis comprised 92% (11/12) and non-atrophic corpus gastritis the remaining 8% (1/12).

The dominating morphological diagnoses in groups 3 plus 4 were atrophic antrum predominant gastritis, 35% (50/145), pangastritis, 24% (35/145), and corpus predominant atrophic gastritis, 20% (29/145). These three subgroups comprised 79% (114/145) of the subjects in groups 3 plus 4. The prevalence of atrophic corpus predominant gastritis was 7% (32/483) in the population, 91% (29/32) of these were obtained in groups 3 plus 4.

Although the preferred embodiment of the method and kit of the invention has been described above in some detail, it should be appreciated that a variety of embodiments will be readily apparent to one skilled in the art. The description of the method and kit of this invention is not intended to be limiting to this invention, but is merely illustrative of the preferred embodiment.

REFERENCES

1. Harris A, Dyspepsia and *Helicobacter pylori*: test, treat or investigate? Eur J Gastroenterol Hepat 1999; 11 (Suppl 1): S31–5.
2. Working Party of the Clinical Services Committee of the British Society of Gastroenterology. Provision of gastrointestinal endoscopy and related services for a district general hospital. Gut 1991; 32: 95–105.
3. Gear M W L, Wilkinson S P, Open access upper alimentary endoscopy. Br J Hosp Med 1989; 41: 438–44.
4. Bodger K, Wyatt J I, Heatley R V, Serologic screening before endoscopy: The value of Helicobacter pylori serology, serum recognition of the CagA and VacA proteins, and serum pepsinogen I, Scand J Gastroenterol 1999; 34: 856–63.
5. Moayyedi P, Zilles A, Clough M, Hemingbrough E, Chalmers D M, Axon A T, The effectiveness of screening and treating *Helicobacter pylori* in the management of dyspepsia, Eur J Gastroenterol Hepatol 1999; 11:1245–50.
6. Chiba N, Lahaie R, Fedorak R N, Bailey R, Veldhuyzen van Zanten S J, Bernucci B, *Helicobacter pylori* and peptic ulcer disease. Current evidence for management strategies, Can Fam Physician 1998; 44: 1481–8.
7. Genta R M, Acid suppression and gastric atrophy: sifting fact from fiction, Gut 1998; 43: 35–8.
8. Coyle W J, Lawson J M, *Helicobacter pylori* infection in patients with early gastric cancer by the endoscopic phenol red test, Gastrointest Endosc 1998; 48: 327–8.
9. Lee B M, Jang J J, Kim J S, You Y C, Chun S A, Kim H S, et al., Association of *Helicobacter pylori* infection with gastric adenocarcinoma, Jpn J Cancer Res 1998; 89: 597–603.
10. Ozasa K, Kurata J H, Higashi A, K. Hayashi K, Inokuchi H, Miki K, et al., *Helicobacter pylori* infection and atrophic gastritis: a nested case-control study in a rural town in Japan, Dig Dis Sci 1999; 44: 253–6.
11. Bech K, Hoier-Madsen M, Feldt-Rasmussen U, Jensen B M, Molsted-Pedersen L, Kuhl C, Thyroid function and autoimmune manifestations in insulin-dependent diabetes mellitus during and after pregnancy, Acta Endocrinol 1991; 124: 534–9.
12. Barrio R, Roldan M B, Alonso M, Canton R, Camarero C, *Helicobacter pylori* infection with parietal cell antibodies in children and adolescents with insulin dependent diabetes mellitus, Pediatr Endocrinol Metab 1997; 10: 511–6.
13. Datta A, Deodhar S D, Datta U, Sehgal S, Non-organ specific & organ specific antibodies in rheumatoid arthritis, Indian J Med Res 1990; 92: 228–32.
14. Mårdh S, Ma J Y, Song Y H, Aly A, Henriksson K, Occurrence of autoantibodies against intrinsic factor, H,K-ATPase and pepsinogen in atrophic gastritis and rheumatoid arthritis. Scand J Gastroenterol 1991; 26: 1089–96.
15. Karlsson A, Burman P, Lööf L, Mårdh S, Major parietal cell antigen in autoimmune gastritis with pernicious anemia is the acid-producing H,K-adenosine triphosphatase of the stomach, J Clin Invest 1988; 81: 475–9.
16. Song Y H, Ma J Y, Mårdh S, Liu T, Sjöstrand S E, Rask L et al., Localization of a pernicious anemia-autoantibody epitope on the a-subunit of the human H,K-ATPase. Scand J Gastroenterol 1994; 29: 122–7.
17. Ma J Y, Borch K, Mårdh S, Human gastric H,K-adenosine triphosphatase β-subunit is a major autoantigen in atrophic corpus gastritis. Expression of the recombinant human glycoprotein in insect cells. Scand J Gastroenterol 1994; 20: 790–4.
18. Baron J H, Clinical tests of gastric secretion: History, Methodology and Interpretation. (1978) London: Macmillan.
19. Samloff I M, Liebman W M, Panitch N M, Serum group I pepsinogens by radioimmunoassay in control subjects and patients with peptic ulcer. Gastroenterol 1975 July; 69(1): 83–90.
20. Samloff IM, Varis K, Ihamaki T, Siurala M, Rotter J I, Relationships among serum pepsinogen I, serum pepsinogen II, and gastric mucosal histology. A study in relatives of patients with pernicious anemia. Gastroenterol 1982 July; 83(1 Pt 2): 204–9.
21. Borch K, Stridsberg M, Burman P, Rehfeld J F, Basal chromogranin A and gastrin concentrations in circulation correlate to endocrine cell proliferation in type A gastritis. Scand J Gastroenterol 1997; 32:198–202.
22. Carmel R, Pepsinogens and other serum markers in pernicious anemia. Am J Pathol 1998; 90: 442–5.
23. Waters H M, Smith C, Howarth J E, Dawson D W, Delamore I W, New enzyme immunoassay for detecting total, type I, and type II intrinsic factor antibodies. J Clin Pathol 1989; 42: 307–12.

24. Mårdh S, Song Y-H, Characterization of antigenic structures in autoimmune atrophic gastritis with pernicious anemia. The parietal cell H,K-ATPase and the chief cell pepsinogen are the two major antigens. Acta Physiol Scand 1989; 136: 581–7.
25. Borch K, Liedberg G, Prevalence and incidence of pernicious anemia. An evaluation for gastric screening. Scand J Gastroenterol 1984; 19: 154–60.
26. Borch K, Jönsson K-Å, Redéen S, Petersson F, Mårdh S, Franzén L, Prevalence of gastroduodenitis and *Helicobacter pylori* infection in the general population: Relations to symptomatology and life style. Dig Dis Sci, 2000, 45: 1322–29.
27. Price A, The Sydney system: Histological division, J Gastroenterol Hepatol 1991; 6: 209–22.
28. Dixon M F, Genta R M, Yardley J H, Correa P, the Participants in the International Workshop on the Histopathology of Gastritis, Houston 1994. Classification and grading of gastritis. The updated Sydney system, Am J Surg Pathol 1996; 20: 1161–81.
29. Karlsson F A, Burman P, Lööf L, Olsson M, Scheynius A, Mårdh S, Enzyme-linked immunosorbent assay of H,K-ATPase, the parietal cell antigen. Clin exp Immunol 1987; 70:604–10.
30. Ma J-Y, Borch K, Sjöstrand SE, Janzon L, Mårdh S, Positive correlation between H,K-adenosine triphosphatase autoantibodies and *Helicobacter pylori* antibodies in patients with pernicious anemia. Scand J Gastroenterol 1994; 29: 961–6.

We claim:

1. A method for diagnosing possible presence of gastritis in a human by evaluating a blood sample, comprising the steps of:
    assaying the blood sample for the presence of antibodies specific for H,K-ATPase,
    assaying the blood sample for the presence of antibodies specific for *Helicobacter pylori*,
    assaying the blood sample for the concentration of pepsinogen I, and
    comparing the presence of H,K-ATPase antibodies, *Helicobacter pylori* antibodies, and pepsinogen I concentration to the respective values of H,K-ATPase antibodies, *Helicobacter pylori* antibodies, and pepsinogen concentration of a normal population, and
    further comprising the steps of multiplying the concentration of pepsinogen I by the concentration of *Helicobacter pylori* antibodies to get a number, and comparing the number to a number calculated similarly for the normal population,
    wherein concentrations of H,K-ATPase antibodies, *Helicobacter pylori* antibodies, and pepsinogen I in the sample and the number obtained by multiplying the concentration of pepsinogen I by the concentration of *Helicobacter pylori* antibodies that are different from respective corresponding values in a normal population are indicative of gastritis.

2. The method according to claim 1, wherein the step of determining the concentrations of H,K-ATPase antibodies, *Helicobacter pylori* antibodies, and pepsinogen I, comprises performing immunoassays for detecting H,K-ATPase antibodies, *Helicobacter pylori* antibodies, and pepsinogen I.

3. The method according to claim 1, wherein a concentration of H,K-ATPase antibodies differing from that of the normal population is indicative of an autoimmune corpus atrophy.

4. The method according to claim 1, wherein a concentration of *Helicobacter pylori* antibodies differing from that of the normal population is indicative of antrum gastritis, or pangastritis.

5. The method according to claim 1, wherein increased concentrations of *Helicobacter pylori* antibodies, and normal to lowered concentrations of pepsinogen I are indicative of atrophy.

6. The method according to claim 1, wherein very low concentrations of pepsinogen I in combination with increased concentrations of H,K-ATPase antibodies are indicative of corpus atrophy.

7. The method according to claim 2, wherein measured concentrations of H,K-ATPase antibodies and *Helicobacter pylori* antibodies which are significantly higher than concentrations in a normal population are indicative of gastritis.

8. The method according to claim 2, wherein a concentration of H,K-ATPase antibodies differing from that of the normal population is indicative of an autoimmune corpus atrophy.

9. The method according to claim 2, wherein a concentration of *Helicobacter pylori* antibodies differing from that of the normal population is indicative of antrum gastritis or pangastritis.

10. The method according to claim 2, wherein increased concentrations of *Helicobacter pylori* antibodies, and normal to lowered concentrations of pepsinogen I are indicative of atrophy.

11. The method according to claim 2, wherein very low concentrations of pepsinogen I in combination with increased concentrations of H,K-ATPase antibodies are indicative of corpus atrophy.

12. The method according to claim 1, wherein measured concentrations of H,K-ATPase antibodies and *Helicobacter pylori* antibodies which are significantly higher than concentrations in the normal population are indicative of gastritis.

* * * * *